United States Patent
Kho et al.

(10) Patent No.: US 7,292,052 B2
(45) Date of Patent: Nov. 6, 2007

(54) DCVG-CIPS MEASURING APPARATUS FOR DETECTING THE RESULTS OF A PIPE LINE

(75) Inventors: Young-Tai Kho, Ansan (KR); Jae-Young Jeon, Anyang (KR); Kyeong-Wan Park, Gwacheon (KR); Yong-Bum Cho, Seoul (KR); Seon-Yeob Li, Ansan (KR); Young-Geun Kim, Ansan (KR)

(73) Assignee: Korea Gas Corporation, Ansan (KR)

(*) Notice: Subject to any disclaimer, the term of this patent is extended or adjusted under 35 U.S.C. 154(b) by 0 days.

(21) Appl. No.: 10/554,060

(22) PCT Filed: Jun. 30, 2003

(86) PCT No.: PCT/KR03/01288

§ 371 (c)(1), (2), (4) Date: Sep. 25, 2006

(87) PCT Pub. No.: WO2004/097460

PCT Pub. Date: Nov. 11, 2004

(65) Prior Publication Data

US 2007/0063713 A1    Mar. 22, 2007

(30) Foreign Application Priority Data

Apr. 26, 2003   (KR) .................. 10-2003-0026551
Apr. 26, 2003   (KR) .................. 10-2003-0026552
Apr. 26, 2003   (KR) .................. 10-2003-0026553
Apr. 26, 2003   (KR) .................. 10-2003-0026554

(51) Int. Cl.
  *G01R 27/08*   (2006.01)

(52) U.S. Cl. ............. 324/700; 324/71.1; 324/71.2
(58) Field of Classification Search ............ 324/700, 324/71.1, 71.2
  See application file for complete search history.

(56) References Cited

U.S. PATENT DOCUMENTS

| | | | |
|---|---|---|---|
| 6,556,027 B2 * | 4/2003 | Banks | 324/700 |
| 6,774,814 B2 * | 8/2004 | Hilleary | 340/870.07 |
| 6,870,356 B2 * | 3/2005 | Murray et al. | 324/71.1 |
| 6,946,855 B1 * | 9/2005 | Hemblade | 324/700 |
| 7,068,052 B2 * | 6/2006 | Hilleary et al. | 324/700 |

* cited by examiner

*Primary Examiner*—Walter Benson
(74) *Attorney, Agent, or Firm*—Fish & Richardson P.C.

(57) ABSTRACT

The present invention relates to a pipeline examination apparatus for Direct Current Voltage Gradient (DCVG) and Closed Interval Potential Survey (CIPS) methods. The pipeline examination apparatus of the present invention detects and analyzes at least one electrode signal while supplying an anticorrosive current to a buried pipeline by switching on and off the anticorrosive current at predetermined intervals. The pipeline examination apparatus includes a signal detection unit and a measurement unit. The signal detection unit detects the electrode signal including a DCVG electrode signal and/or a CIPS electrode signal. The measurement unit receives the electrode signal from the signal detection unit and analyzes the electrode signal. The measurement unit includes a measurement method selection unit, a control unit, a storage unit, an analysis unit and a display unit.

3 Claims, 5 Drawing Sheets

[Fig. 1]
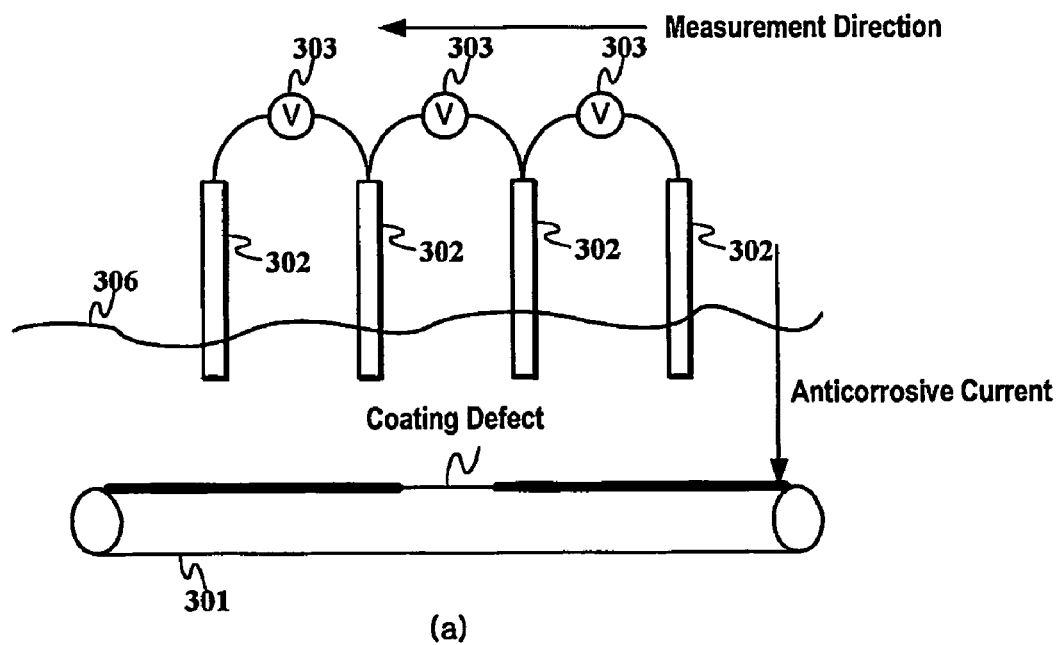
(a)
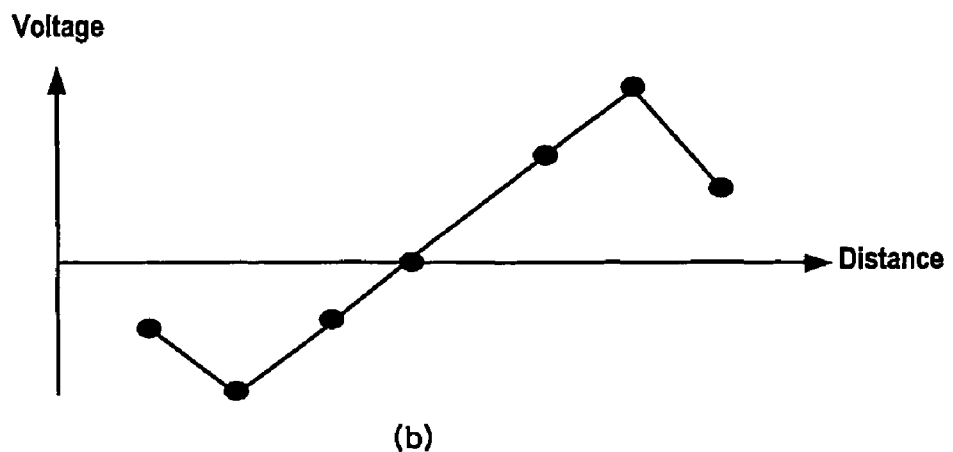
(b)

[Fig. 2]
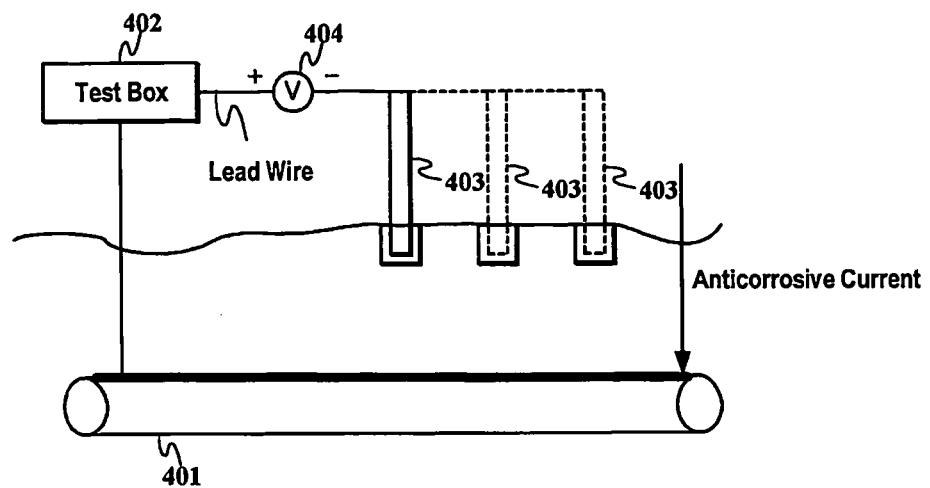
[Fig. 3]
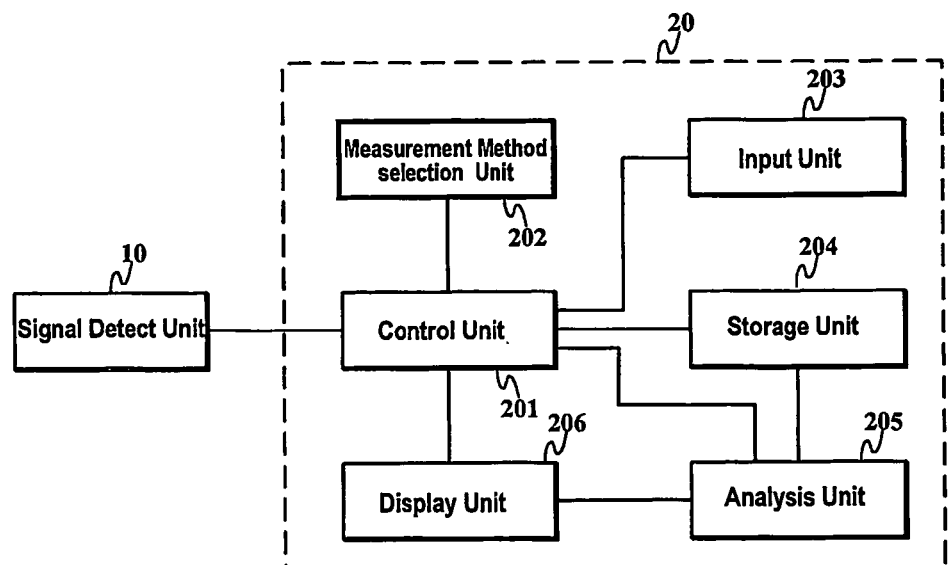

[Fig. 4]
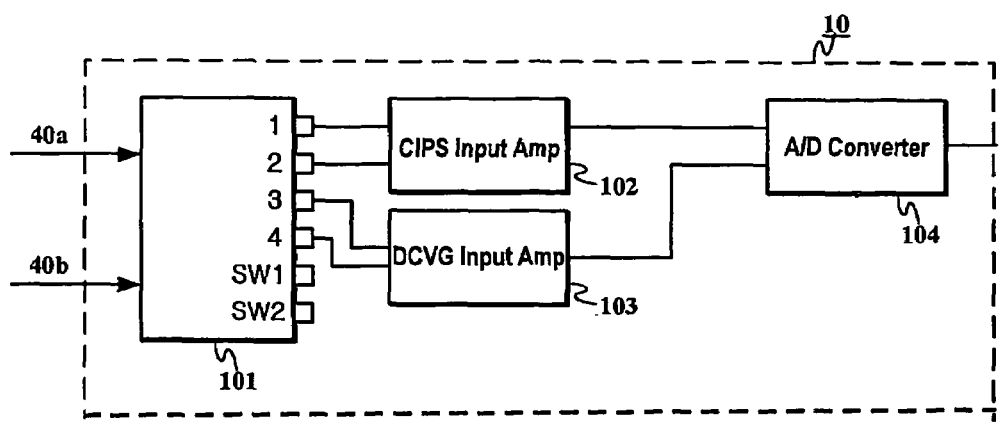

DCVG-CIPS MEASURING APPARATUS FOR DETECTING THE RESULTS OF A PIPE LINE

TECHNICAL FIELD

The present invention relates, in general, to a pipeline examination apparatus for direct current voltage gradient and closed interval potential survey methods, which analyzes and displays examination results obtained through both a direct current voltage gradient method of detecting coating defect parts on a buried pipeline without the need for excavation, and a closed interval potential survey method of surveying the corrosion protection and coating states of the buried pipeline.

BACKGROUND ART

Of methods of detecting coating defect parts on a buried pipeline, a Direct Current Voltage Gradient (DCVG) technique, which is known as a method having the highest precision, is adapted to discover the coating detect parts by detecting the deformation of a potential distribution appearing on the soil around the coating defect parts at the time of detecting the coating defect parts, which may result from mechanical defects during the burying of the pipeline, or damages caused by other constructions. A Closed Interval Potential Survey (CIPS) method is adapted to survey the corrosion protection and coating states of a buried pipeline by connecting a measurement wire to a lead wire of the buried pipeline and measuring the potential of a portion immediately above the pipeline while moving a reference electrode along the buried pipeline at regular intervals (several meters). The DCVG and the CIPS methods are performed while a rectifier for corrosion protection is switched on/off to the buried pipeline.

For an apparatus for measuring data using the above two methods, that is, the DCVG and CIPS methods, there has been used an Electric Pen Recorder (EPR), which is a device for recording, using a pen, continuously measured values on a paper in the form of analog data. In the prior art, an operation is performed in such a way that an operator determines accurate values by reading contents measured in a field with the naked eye using the EPR, records the accurate values using a writing tool, returns to an office, and arrange the measured values.

Recently, besides the apparatus using the EPR, apparatuses for converting values measured in a field into digital data, and then arranging and displaying the digital data have been developed. However, such apparatuses are problematic in that, since they employ small-sized Liquid Crystal Display (LCD) panels, the apparatuses cannot display continuously measured values on the LCD panels, and, additionally, it cannot display previously measured values in the form of accumulative data.

DISCLOSURE OF THE INVENTION

Accordingly, the present invention has been made keeping in mind the above problems occurring in the prior art, and an object of the present invention is to provide a pipeline examination apparatus for DCVG and CIPS methods, which measures and arranges a DCVG electrode signal and a CIPS electrode signal of a buried pipeline, displays the arranged electrode signals, and measures and displays a continuous potential distribution.

Another object of the present invention is to provide a portable examination apparatus, which can display examination results in a field or immediately ascertain the examination results through print.

In order to accomplish the above objects, the present invention provides a pipeline examination apparatus for Direct Current Voltage Gradient (DCVG) and Closed Interval Potential Survey (CIPS) methods, which detects and analyzes at least one electrode signal while supplying an anticorrosive current to a buried pipeline by switching on and off the anticorrosive current at predetermined intervals, comprising a signal detection unit detecting the electrode signal including a DCVG electrode signal and/or a CIPS electrode signal, and a measurement unit receiving the electrode signal from the signal detection unit and analyzing the electrode signal, wherein the measurement unit comprises a measurement method selection unit selecting any or both of the DCVG electrode signal and the CIPS electrode signal to be detected by the signal detection unit, a control unit receiving the electrode signal from the signal detection unit, a storage unit storing the electrode signal received by the control unit, a analysis unit analyzing the electrode signal stored in the storage unit, and a display unit displaying the electrode signal received by the control unit and analysis results obtained from the analysis unit, and wherein the control unit controls the signal detection unit to detect the electrode signal on the basis of selection of the measurement method selection unit, and controls storage, analysis and display of the electrode signal.

Preferably, the measurement unit may be a touch-screen type Personal Digital Assistant (PDA), and the signal detection unit and the measurement unit may communicate with each other through a serial or parallel interface.

Preferably, the measurement method selection unit may select a pulse period of the electrode signal received by the control unit so that the pulse period is synchronized with an ON/OFF period of the anticorrosive current.

Preferably, the analysis of the electrode signal may be performed by sequentially extracting a magnitude of the electrode signal stored in the storage unit over time, and the display unit displays the sequential electrode signal over time.

Preferably, the measurement unit may further comprise an output unit capable of outputting the analysis results.

BRIEF DESCRIPTION OF THE DRAWINGS

FIG. 1 illustrates the detection of a coating defect part on a pipeline using a DCVG method;

FIG. 2 illustrates the detection of the corrosion protection state of the pipeline using a CIPS method;

FIG. 3 illustrates the construction of an examination apparatus 1 according to an embodiment of the present invention;

FIG. 4 illustrates the construction of a signal detection unit 10 according to an embodiment of the present invention;

BEST MODE FOR CARRYING OUT THE INVENTION

Figure 5:
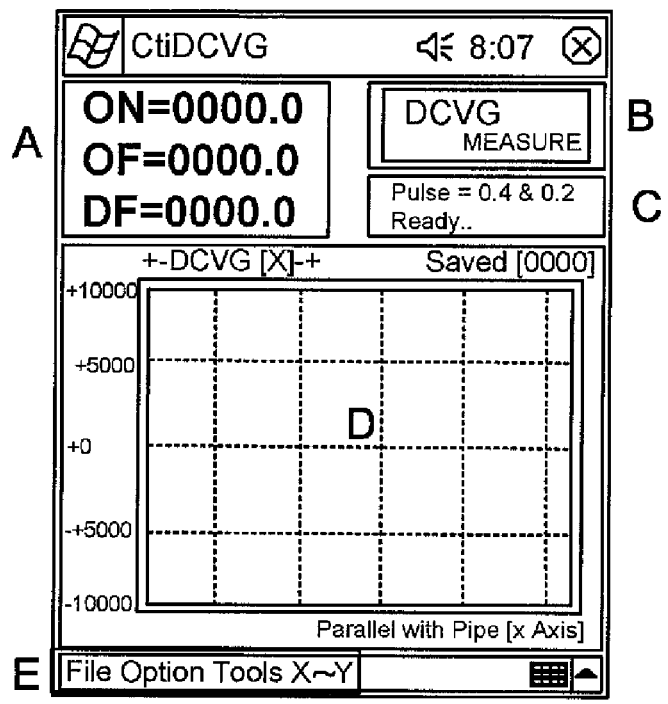
FIG. 5 illustrates the screen of a measurement unit 20 according to an embodiment of the present invention.

Hereinafter, embodiments of the present invention will be described in detail with reference to the attached drawings.

First, the detection of a coating defect part on a buried pipeline using a DCVG method and the detection of electrical corrosion protection state of the buried pipeline using a CIPG method are described with reference to FIGS. 1 and 2.

FIG. 1 illustrates an example of the detection of a coating detect part using a DCVG method. The DCVG method, which is a method to detect a coating defect part by measuring a voltage gradient occurring around a buried pipeline 301 when an anticorrosive current is applied to the buried pipeline 301, spaces two saturated copper sulfate reference electrodes 302 apart from each other by about 1 to 2 m along the portion immediately above the buried pipeline 301, and then measures a potential difference between the two reference electrodes 302, that is, a voltage gradient on a surface 306, using a voltmeter 303. In this case, the anticorrosive current applied to the pipeline 301 is periodically switched on and off, and a potential difference, obtained when the current is switched off, is corrected on the basis of a potential difference, obtained when the current is switched on, thus accurately measuring the voltage gradient. As shown in FIG. 1b, the anticorrosive current is concentrated on a coating defect part having the lowest resistance, so that a high potential gradient around the coating defect part is generated. Therefore, when a potential is measured on the surface 306 along the pipeline in a longitudinal direction using the two reference electrodes 302, there occurs a phenomenon in which the polarity of <ON potential-OFF potential> is reversed around the coating defect part, as shown in FIG. 1b, so that it can be seen that a reverse position corresponds to the coating defect part.

FIG. 2 illustrates an example of the detection of the electric corrosion protection state of a buried pipeline using a CIPS method. A lead wire of a pipeline 401 is connected to a positive (+) terminal of a voltmeter 404 and a reference electrode 403 is connected to a negative (−) terminal of the voltmeter 404. An anticorrosive potential of the pipeline 401 is measured at intervals of about 2 to 4 m while the lead wire of the pipeline is being drawn. A value to be measured at a single point may include an ON potential, an OFF potential, ON potential-OFF potential, etc. The ON and OFF potentials are based on whether or not the anticorrosive current is applied. Fundamentally, the electrical corrosion protection state of the buried pipeline 401 can be surveyed on the basis of the ON potential. However, in this case, since an error may occur due to the resistivity of the soil itself, an OFF potential is measured together with the ON potential to eliminate this error.

FIG. 3 illustrates a block diagram of a pipeline examination apparatus for DCVG and CIPS methods according to an embodiment of the present invention. Referring to FIG. 3, an examination apparatus 1 includes a signal detection unit 10, and a measurement unit 20 comprised of a control unit 201, a measurement method selection unit 202, an input unit 203, a storage unit 204, an analysis unit 205 and a display unit 206. Further, the signal detection unit 10 and the measurement unit 20 communicate with each other through a serial or parallel interface.

The signal detection unit 10 detects an electrode signal, including a DCVG electrode signal and a CIPS electrode signal, using a probe. Each of the electrode signals is input to the control unit 201 through an amplification and Analog/Digital (A/D) conversion process. FIG. 4 illustrates a detailed block diagram of the signal detection unit. Referring to FIG. 4, the signal detection unit 10 includes a measured value input unit 101, a CIPS input amplifier 102, a DCVG input amplifier 103, and an A/D converter 104.

The measured value input unit 101 is connected to both a CIPS electrode 40a and a DCVG electrode 40b, and outputs a CIPS electrode signal, a DCVG electrode signal, and a CIPS-DCVG electrode signal to the input amplifiers 102 and 103 according to the state of switches SW1 and SW2. For example, if the switches SW1 and SW2 are ON and OFF, respectively, the measured value input unit 101 outputs only a CIPS electrode signal to the CIPS input amplifier 102. If they are OFF and ON, respectively, the measured value input unit 101 outputs only a DCVG electrode signal to the DCVG input amplifier 103. Further, if they are ON and ON, respectively, the measured value input unit 101 simultaneously outputs the CIPS electrode signal and the DCVG electrode signal to the CIPS input amplifier 102 and DCVG input amplifier 103, respectively.

In the meantime, the CIPS electrode signal is input to first and second terminals of the measured value input unit 101, and the DCVG electrode signal is input to the third and fourth terminals of the measured value input unit 101.

The input amplifiers 102 and 103 are devices for amplifying the input values of the CIPS and DCVG electrode signals, and preferably employ different amplification schemes to prevent interference from occurring between the CIPS and DCVG electrode signals. For example, preferably, the CIPS input amplifier 102 employs an emitter follower amplifier, and the DCVG input amplifier 103 employs a differential input amplifier.

The A/D converter 104 is a device that converts analog amplified signals received from the input amplifiers 102 and 103 into digital signals. A 22-bit A/D converter ADS1213 of Burr Brown Corporation is used as the A/D converter 104. Further, the A/D converter 104 outputs the digital signals to the control unit 201.

The control unit 201 receives electrode signals from the signal detection unit 10. The measurement method selection unit 202 selects whether electrode signals to be detected by the signal detection unit 10 are any or both of a DCVG electrode signal and a CIPS electrode signal. Therefore, the measurement method selection unit 202 selects a measurement method by controlling the states of the switches SW1 and SW2. In the meantime, each of the electrode signals must be input to the measurement unit 20 in synchronization with the ON/OFF period of the anticorrosive current applied to the buried pipeline. The measurement method selection unit 202 selects a pulse period to allow the pulse period of the electrode signals received by the control unit 201 to be synchronized with the ON/OFF period of the anticorrosive current.

The storage unit 204 sequentially stores the electrode signals received by the control unit 201 over time. The analysis unit 205 analyzes the electrode signals stored in the storage unit 204. For example, the analysis unit 205 performs the analysis by extracting the magnitudes of the sequentially stored electrode signals from the storage unit 204 over time. The display unit 206 displays the electrode signals received by the control unit 201, displays the electrode signals analyzed by the analysis unit 205, and, in detail, sequentially displays the magnitudes of the electrode signals. The control unit 201 controls various operations, such as the storage, analysis and display of the electrode signals input to the control unit, as well as the selective detection of the electrode signals performed through the signal detection unit, depending on the input signals applied to the input unit 203.

Further, the analysis results obtained from the measurement unit 20 may be transmitted to an output unit (not shown) and output thereby. At this time, a typical small-sized printer may be used as the output unit whereby there is an advantage in that a measurer can immediately output the results measured in a field using the printer, and then ascertain the measurement results.

FIG. 5 illustrates an example of the screen of the measurement unit 20. A touch-screen input type Personal Digital Assistant (PDA) may be used as the measurement unit 20. Region A on the screen is used to display measurement results, in which a result value is displayed after a measurement has been completed once. By pressing the region A, a single measurement point can be stored in the storage unit 204. If region B is pressed, a measurement screen and a trend screen (screen to sequentially view stored data over time) are switched over. Region C is used to display the period of a current pulse, a measurement-related message, etc., and region D is used to display a measurement graph and the measurement starts when the region D is pressed. Region E is used to select a menu item related to parameter setting.

In detail, 'ON=0.0000' in the region A indicates an ON potential value obtained while an anticorrosive current flows through a pipeline, 'OF=0.0000' indicates an OFF potential value obtained while the anticorrosive current doesn't flow through the pipeline, and 'DF=0.0000' indicates a difference between ON and OFF potentials.

Figure 6:
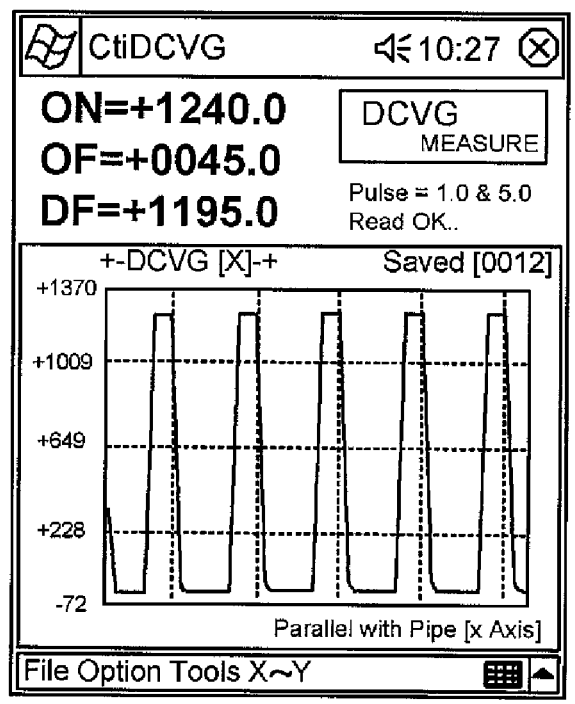
FIG. 6 illustrates an example of a screen showing current results measured using the DCVG method among examples of the screen of the measurement unit 20.
Figure 7:
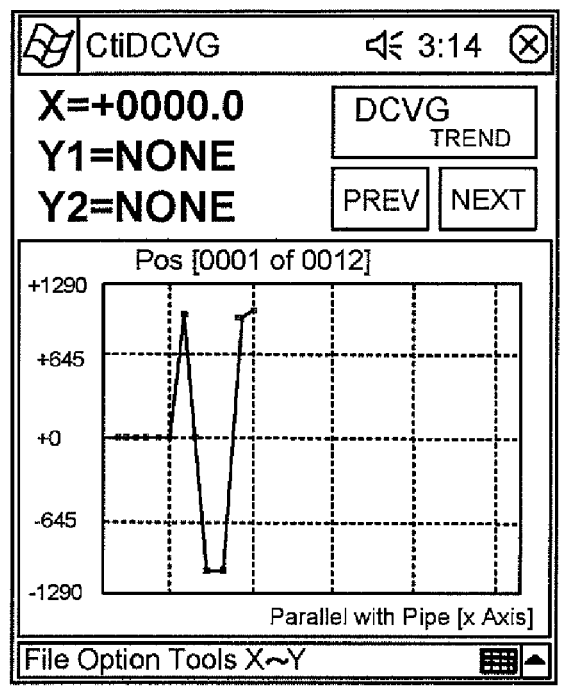
FIG. 7 illustrates an example of a screen sequentially showing the most recent results obtained by measurements using the DCVG method among examples of the screen of the measurement unit 20.

An item 'DCVG Measure' in the region B indicates that a pulse currently being measured is displayed in a region D when the measurement is performed using the DCVG method, and an item 'DCVG Trend' indicates that measurement data, stored prior to the completion of the current measurement, are displayed in the region D. Items 'CIPS Measure' and 'CIPS Trend' are similar to the 'DCVG Measure' and 'DCVG Trend', respectively, and indicate that the results measured using the CIPS method are displayed in the region D. FIG. 6 illustrates an example of the screen in the 'DCVG Measure' state, and FIG. 7 illustrates an example of the screen in the 'DCVG Trend' state.

An item 'Pulse=0.4&0.2' in the region C indicates a pulse period synchronized with the period for switching on and off the anticorrosive current to the pipeline, in which the former 0.4 indicates an ON period and the latter 0.2 indicates an OFF period. Moreover 0.4&0.2, there are several types of usable pulse periods, such as 1.0&0.5, 2.0&1.0, 3.0&1.5, and 4.0&2.0. In the meantime, the ON and OFF operations of the anticorrosive current are performed using equipment called a "rectifier interrupter". 'Pulse' is synchronized on the basis of the ON/OFF period set by the rectifier interrupter. An item 'Ready . . . ' indicates that a measurement is ready to start. If the region D is pressed to start the measurement, a message 'Wait . . . ' is briefly displayed, and then a message 'Processing . . . ' is displayed. At this time, the pipeline examination apparatus 1 reads data.

An item 'DCVG[X]' on another region indicates that a measurement is performed in the direction of extension of the pipeline when the measurement is performed using the DCVG method. When a potential reverse position is detected during the measurement, an item 'X~Y' is pressed on menu items, so that a measurement direction is changed from an X axis to a Y axis (vertical direction to the pipeline) and then the measurement is performed. Further, an item 'Saved [0000]' indicates the number of pieces of data stored, and an item 'Parallel with Pipe [X axis]' indicates that the measurement is performed in the direction of extension of the pipeline when the measurement is performed using the DCVG method. The message 'Parallel with Pipe [X axis]' is changed to a message ' Across Pipe' when the measurement direction is changed to the vertical direction to the pipeline.

Hereinafter, the operation of performing measurement and analysis using the pipeline examination apparatus 1 according to an embodiment of the present invention is described. First, regardless of the DCVG or CIPS method, an anticorrosive current should be allowed to flow through a buried pipeline before a measurement is taken. At this time, if the anticorrosive current is supplied from a rectifier to the buried pipeline and then corrosion protection is performed on the buried pipeline, a wire connected from the rectifier to the pipeline is disconnected, and then connected to a rectifier interrupter, and the ON/OFF times of the anticorrosive current are set by the rectifier interrupter.

In the meantime, in the case where a measurement is required to be performed during an interval when a sacrificial anode method is used, negative electricity should be supplied to the pipeline using an external power supply and interrupter combination and switched on or off at regular intervals. At this time, a temporary anode should be buried. For the temporary anode, a copper rod included in the pipeline examination apparatus is generally used, otherwise the railway of a train or other steel-frame structures may be used by suitably utilizing a surrounding geographical structure. In this case, as a distance between the temporary anode and the pipeline becomes longer, a range in which the measurement can be performed becomes wide. Therefore, the distance between the pipeline and the temporary anode is preferably at least 50 m, and most preferably loom or longer. In this case, the ON and OFF times of the anticorrosive current are set by the external power supply and interrupter combination.

Figure 8:
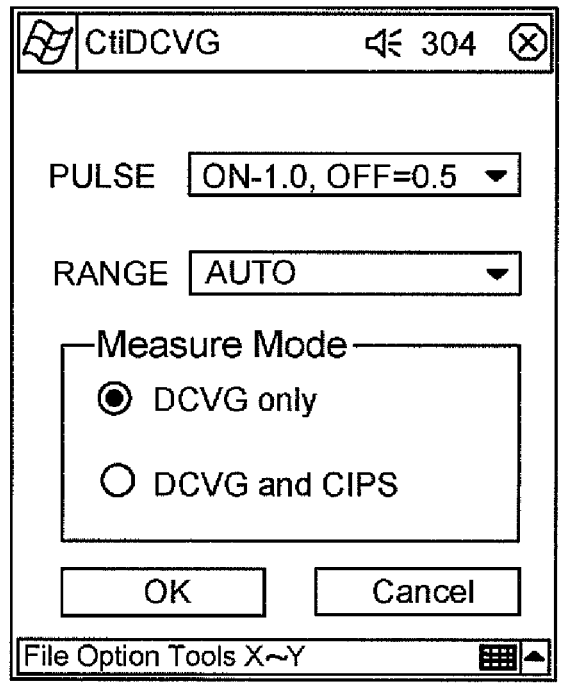
FIG. 8 illustrates an example of a screen displayed when an 'Option' item of FIG. 5 is pressed.

Next, the measurer activates a dialog screen as shown in FIG. 8 by pressing an 'Option' menu item in the region E of FIG. 5, synchronizes 'PULSE' with the ON/OFF times of the anticorrosive current, and then sets 'Measure Mode'. When the DCVG electrode signal is selected, 'DCVG' mode is selected, while when the CIPS electrode signal is selected, 'DCVG and CIPS' mode is selected.

When the pipeline examination apparatus 1 simultaneously receives the DCVG and CIPS electrode signals from the signal detection unit 10, the measurer can display four modes in the region D by pressing the region B of FIG. 7. The measurer presses the region D of FIG. 7 to start the measurement, and presses the region A of FIG. 7 to store measurement results when the measurement has been completed.

INDUSTRIAL APPLICABILITY

According to the present invention, there are advantages in that a DCVG electrode signal and a CIPS electrode signal of a buried pipeline are detected, and the detected electrode signals are displayed, or the detected electrode signals are stored and the magnitudes thereof are sequentially displayed over time, so that measurement results can be obviously ascertained.

Further, the present invention is advantageous in that it can provide a portable examination apparatus using a Personal Digital Assistant (PDA), thus displaying or analyzing measurement results in a field, and immediately ascertaining the measurement results through print.

The invention claimed is:

1. A pipeline examination apparatus for Direct Current Voltage Gradient (DCVG) and Closed Interval Potential Survey (CIPS) methods, which detects and analyzes at least one electrode signal while supplying an anticorrosive current to a buried pipeline by switching on and off the anticorrosive current at predetermined intervals, comprising:
   a signal detection unit detecting the electrode signal including a DCVG electrode signal and/or a CIPS electrode signal; and
   a measurement unit receiving the electrode signal from the signal detection unit and analyzing the electrode signal,
   wherein the signal detection unit comprises:
      a measured value input unit receiving a DCVG electrode signal measured using a DCVG method and a CIPS electrode signal measured using a CIPS method through one or more probes, the measured value input unit including switching means that switches over an operation of selectively receiving the DCVG electrode signal and the CIPS electrode signal and an operation of simultaneously receiving the DCVG electrode signal and the CIPS electrode signal;
      a DCVG input amplifier amplifying an input value of the DCVG electrode signal;
      a CIPS input amplifier amplifying an input value of the CIPS electrode signal; and
      an Analog/Digital (A/D) converter converting analog signals received from the DCVG input amplifier and the CIPS input amplifier into digital signals,
   wherein the measurement unit comprises:
      a measurement method selection unit selecting any or both of the DCVG electrode signal and the CIPS electrode signal to be detected by the signal detection unit;
      a control unit receiving the electrode signal from the signal detection unit;
      a storage unit storing the electrode signal received by the control unit;
      an analysis unit analyzing the electrode signal stored in the storage unit; and
      a display unit displaying the electrode signal received by the control unit and analysis results obtained from the analysis unit; and
   wherein the control unit controls the signal detection unit to detect the electrode signal on the basis of selection of the measurement method selection unit, and controls storage, analysis and display of the electrode signal.

2. The pipeline examination apparatus according to claim 1, wherein the DCVG and CIPS input amplifiers employ different amplification schemes.

3. The pipeline examination apparatus according to claim 1, wherein the DCVG input amplifier employs an emitter follower amplification scheme and the CIPS input amplifier employs a differential input amplification scheme.

* * * * *